(12) United States Patent
Park et al.

(10) Patent No.: US 7,778,700 B2
(45) Date of Patent: Aug. 17, 2010

(54) BRAIN WAVE MEASURING METHOD, APPARATUS AND COMPUTER READABLE RECORDING MEDIUM IMPLEMENTED WITH PROGRAM FOR EXECUTING THE METHOD

(75) Inventors: Hyun Wook Park, Daejeon (KR); Sung Suk Oh, Daegu (KR); Jun-Young Chung, Incheon (KR)

(73) Assignee: Korea Advanced Institute of Science & Technology (KR)

( * ) Notice: Subject to any disclaimer, the term of this patent is extended or adjusted under 35 U.S.C. 154(b) by 500 days.

(21) Appl. No.: 11/745,586

(22) Filed: May 8, 2007

(65) Prior Publication Data

US 2008/0234596 A1 Sep. 25, 2008

(30) Foreign Application Priority Data

Mar. 21, 2007 (KR) .................. 10-2007-0027681

(51) Int. Cl.
*A61B 5/05* (2006.01)
(52) U.S. Cl. ...................... 600/544; 600/545
(58) Field of Classification Search .......... 600/544–546
See application file for complete search history.

(56) References Cited

U.S. PATENT DOCUMENTS

| 4,716,907 | A  | * | 1/1988  | Nakamura et al. | ........... | 600/544 |
| 5,792,069 | A  | * | 8/1998  | Greenwald et al. | ........... | 600/544 |
| 7,282,028 | B2 | * | 10/2007 | Kim et al. | ................... | 600/300 |
| 2006/0135881 | A1 | * | 6/2006  | Giftakis et al. | .............. | 600/544 |
| 2006/0149139 | A1 | * | 7/2006  | Bonmassar et al. | ......... | 600/300 |

* cited by examiner

*Primary Examiner*—Robert L Nasser
*Assistant Examiner*—Michael D'Angelo
(74) *Attorney, Agent, or Firm*—The Belles Group, P.C.

(57) ABSTRACT

A method for measuring a brain wave comprises extracting positive and negative peaks from an electrocardiogram (EKG) signal reflecting heartbeat information, and positive peaks from an electroencephalogram (EEG) signal reflecting heartbeat-caused noise information and brain wave information. The positive peaks of the EEG signal are classified into a first peak group and a second peak group based on the positive peaks of the EKG signal. The first peak group is affected more greatly by the heartbeat than by the brain wave, and the second peak group is affected more greatly by the brain wave than by the heartbeat. Noise of the first and second peak groups is removed from the EEG signal.

24 Claims, 2 Drawing Sheets

BRAIN WAVE MEASURING METHOD, APPARATUS AND COMPUTER READABLE RECORDING MEDIUM IMPLEMENTED WITH PROGRAM FOR EXECUTING THE METHOD

This nonprovisional application claims priority under 35 U.S.C. §119(a) on Patent Application No. 10-2007-0027681 filed in Republic of Korea on Mar. 21, 2007, the entire contents of which are hereby incorporated by reference.

FIELD OF THE INVENTION

This document relates to a method and apparatus for measuring a brain wave, and a computer readable recording medium implemented with a program for executing the brain wave measuring method.

Various medical machinery and instruments are being used in current clinical fields. In particular, a magnetic resonance imaging (MRI) apparatus provides an image excellent in spatial resolution as compared with other medical apparatuses. One distinctive characteristic of this MRI apparatus is that a brain shape of a human is examined in detail to help clinical treatments or researches on brain functions. However, such an image provided by MRI with the excellent spatial resolution has poor temporal resolution. On the other hand, an electroencephalogram (EEG) is being widely used in interictal epileptiform discharge (IED) or sleep studies due to its high temporal resolution. However, the EEG is disadvantageous of spatial resolution, leading to a difficulty in studying spatial characteristics of brains. For this reason, current researches are underlined to complement the disadvantages of the MRI and the EEG and combine the advantages thereof using both the MRI that has high spatial resolution and the EEG that has high temporal resolution. Exploring how MRI measurement and EEG measurement each are performed is necessary to obtain simultaneously performed MRI and EEG measurement. In the case of MRI, a patient who does not possess any metal lies in a bed in an MRI room, while the patient's brain is fixed to the bed, and the MRI measurement proceeds. In the case of EEG, a patient wears an EEG cap, and electrical signals transmitted through cables connected to the EEG cap are measured. For the simultaneously performed MRI and EEG measurement, a patient who wears an EEG cap lies in a bed in an MRI room, and the MRI measurement and the EEG measurement proceed simultaneously. However, when the MRI and EEG measurements are performed simultaneously using two different apparatuses, some artifacts are often observed in contrast to the case of the individually performed MRI and EEG measurements using two apparatuses separately. One severe artifact includes ballistocardiac artifacts (BAs) observed in EEG data due to heartbeats of a patient.

Various algorithms are proposed to remove such BAs. Exemplary algorithms include a mean subtraction method, an adaptive filtering method, an independent component analysis (ICA), and a principle component analysis (PCA).

According to the mean subtraction method, BAs appearing at a period nearly the same as a heartbeat in an EEG signal are averaged, and this averaged BA value is subtracted from the EEG signal in accordance with the heartbeat so as to remove the BAs. Averaging the BAs requires finding out a moment at which the heartbeat is generated, and the BAs appearing in the EEG signal after the heartbeat is generated. An electrocardiogram (EKG) is used as a reference signal to find out the heartbeat generation moment. The EKG measurement is performed at the same time of the EEG measurement. The EKG measurement represents an accurate heartbeat since an EKG measures an electrical activity of the heart at the aorta that branches out of the heart. The heartbeat generation moment uses an R peak among P_QRS_T peaks appearing when the heartbeat is generated. Also, assuming that a BA appear in the EEG signal after a fixed period of time from the moment at which each heartbeat is generated, each BA is discovered after a fixed period of time after the individual heartbeats. The temporal size of the BAs taken for the average BA value, i.e., window size, uses an average value of time differences between neighboring R peaks. As described above, this mean subtraction method can be characterized by using an EKG signal as a reference signal, using an average BA when BAs in an EEG signal are removed, and using BAs each with a fixed window size after a fixed period from a moment at which an R peak is generated in the EKG signal due to the heartbeat in order to calculate the average BA value in the EEG signal. The mean subtraction method is applied with the assumption that each BA appears with a fixed window size after a fixed period of time after the heart beats. However, a heartbeat of a test object (e.g., a patient) may not affect an EEG signal in every fixed period of time, and the heart may not always beat regularly. Thus, the window size of the BA and period of time after the heart beats may not always be the same. As a result, the mean subtraction method may not be effective on the BA removal.

An adaptive filtering method uses an EKG signal as a reference signal as like the mean subtraction method. In other words, according to the adaptive filtering method, signal components including BAs appearing in an EEG signal are estimated from an EKG signal, and these signal components are subtracted from the original EEG signal so as to remove the BAs. However, the adaptive filtering method needs to set a filter coefficient for a filtering activity. As the filter coefficient increases, an amount of required computation is likely to increase exponentially.

On the basis of PCA and ICA, an EEG signal is obtained from the combination of several signals. In the case of ICA, an EEG signal is divided into independent components. One difference of PCA from the ICA lies in that the EEG signal is divided into principal components. After the division of the EEG signal according to each of the ICA and PCA, those components that are seemingly related to BAs are directly screened among the divided components and removed thereafter. When the screened components are removed, the BA-related components and the number thereof can be set to certain values manually. After the removal, the remaining components are combined to obtain an EEG signal without the BAs. However, according to the ICA and PCA, a user directly screens those seemingly BA-related components. Thus, the subjective view of the user could be reflected on the BA removal procedure, and the resultant components after the ICA and PCA may not be determined accurately. This inaccuracy may provoke the resultant signal removed of the BAs to distort an actual EEG signal. Also, when the EEG signal is restored after the removal of the components, the restored EEG signal may be an artificially distorted signal instead of an actually measured EEG signal.

SUMMARY

An aspect of this document is to provide a brain wave measuring method advantageous of minimizing noise generated by heartbeats of a test object (e.g., patient).

Another aspect of the present invention is to minimize noise, which is generated due to heartbeats of a test object, when a brain wave pattern of the test object is measured using a magnetic resonance imaging (MRI) apparatus and a electroencephalogram (EEG) apparatus.

Another aspect of the present invention is to effectively remove noise generated due to heartbeats despite of irregularity in heartbeats.

Another aspect of the present invention is to reduce an amount of computation during a procedure of removing noise generated due to heartbeats so as to shorten a measurement time of a brain wave.

In an aspect, a method for measuring a brain wave comprises extracting positive and negative peaks from an electrocardiogram (EKG) signal reflecting heartbeat information, and positive peaks from an electroencephalogram (EEG) signal reflecting heartbeat-caused noise information and brain wave information, classifying the positive peaks of the EEG signal into a first peak group and a second peak group based on the positive peaks of the EKG signal, wherein the first peak group is affected more greatly by the heartbeat than by the brain wave and the second peak group is affected more greatly by the brain wave than by the heartbeat, and removing noise of the first and second peak groups from the EEG signal.

The positive peaks of the EKG signal may include R peaks, and the R peaks may be extracted by a k-TEO method.

The negative peaks of the EKG signal may have a minimum value between the two adjacent R peaks.

Classifying the EEG signal may comprise classifying the positive peaks of the EEG signal into the first peak group and the second peak group according to an average value and a standard deviation of temporal distances between the adjacent positive peaks of the EKG signal.

Removing the noise may comprise generating window sizes over a time axis for every positive peak of the EKG signal based on the positive and negative peaks of the EKG signal, calculating time differences between the peaks included in the first peak group and the positive peaks of the EKG signal temporally most close to the peaks included in the first peak group, calculating an average value of ballistocardiac artifacts (BAs) of the peaks included in the first peak group, removing a first noise by subtracting the average BA value of the first peak group from the peaks included in the first peak group according to the window sizes and the time differences corresponding to the peaks included in the first peak group, and removing a second noise by subtracting the average BA value of the first peak group from the peaks included in the second peak group according to an average value of the window sizes and an average value of the time differences.

Generating the window sizes may comprise setting the window sizes to be the triple the respective temporal distances between the positive peaks of the EKG signal and the negative peaks most close to the positive peaks of the EKG signal.

The positive peaks of the EKG signal may be allocated individually at a point being a first one-third portion of the corresponding window sizes.

Removing the first noise may comprise subtracting the average BA value of the first peak group of the window sizes corresponding to the peaks included in the first peak group from the peaks included in the first peak group by delaying the first peak group average BA value from the positive peaks of the EKG signal as much as the respective time differences.

In another aspect, an apparatus for measuring a brain wave comprises a peak information extractor extracting positive and negative peaks from an electrocardiogram (EKG) signal reflecting heartbeat information, and positive peaks from an electroencephalogram (EEG) signal reflecting heartbeat-caused noise information and brain wave information, an EEG signal classifier classifying the positive peaks of the EEG signal into a first peak group and a second peak group based on the positive peaks of the EKG signal, wherein the first peak group is affected more greatly by the heartbeat than by the brain wave and the second peak group is affected more greatly by the brain wave than by the heartbeat, and a noise remover removing noise of the first and second peaks groups from the EEG signal.

The positive peaks of the EKG signal may include R peaks, and the R peaks may be extracted by a k-TEO method.

The negative peaks of the EKG signal may have a minimum value between the two adjacent R peaks.

The EEG signal classifier may classify the positive peaks of the EEG signal into the first peak group and the second peak group according to an average value and a standard deviation of temporal distances between the adjacent positive peaks of the EKG signal.

The noise remover may comprise a window size generation block generating window sizes over a time axis for every positive peak of the EKG signal based on the positive and negative peaks of the EKG signal, a time difference calculation block calculating time differences between the peaks included in the first peak group and the positive peaks of the EKG signal temporally most close to the peaks included in the first peak group, an average ballistocardiac artifact (BA) calculation block calculating an average value of BAs of the peaks included in the first peak group, a first noise removal block removing a first noise by subtracting the average BA value of the first peak group from the peaks included in the first peak group according to the window sizes and the time differences corresponding to the peaks included in the first peak group, and a second noise removal block removing a second noise by subtracting the average BA value of the first peak group from the peaks included in the second peak group according to an average value of the window sizes and an average value of the time differences.

The window sizes generated in the window size generation block may be triple the respective temporal distances between the positive peaks of the EKG signal and the negative peaks most close to the positive peaks of the EKG signal.

The positive peaks of the EKG signal may be allocated individually at a point being a first one-third portion of the corresponding window sizes.

The first noise removal block may subtract the average BA value of the first peak group of the window sizes corresponding to the peaks included in the first peak group from the peaks included in the first peak group by delaying the first peak group average BA value from the positive peaks of the EKG signal as much as the respective time differences.

In another aspect, a computer readable recording medium implemented with a program for executing a brain wave measuring method comprises a first instruction of extracting positive and negative peaks from an electrocardiogram (EKG) signal reflecting heartbeat information, and positive peaks from an electroencephalogram (EEG) signal reflecting heartbeat-caused noise information and brain wave information, a second instruction of classifying the positive peaks of the EEG signal into a first peak group and a second peak group based on the positive peaks of the EKG signal, wherein the first peak group is affected more greatly by the heartbeat than by the brain wave and the second peak group is affected more greatly by the brain wave than by the heartbeat, and a third instruction of removing noise of the first and second peaks groups from the EEG signal.

The positive peaks of the EKG signal may include R peaks, and the R peaks may be extracted by a k-TEO method.

The negative peaks of the EKG signal may have a minimum value between the two adjacent R peaks.

The second instruction of classifying the EEG signal may comprise classifying the positive peaks of the EEG signal into the first peak group and the second peak group according to an average value and a standard deviation of temporal distances between the adjacent positive peaks of the EKG signal.

The third instruction of removing the noise may comprise generating window sizes over a time axis for every positive peak of the EKG signal based on the positive and negative peaks of the EKG signal, calculating time differences between the peaks included in the first peak group and the positive peaks of the EKG signal temporally most close to the peaks included in the first peak group, calculating an average value of ballistocardiac artifacts (BAs) of the peaks included in the first peak group, removing a first noise by subtracting the average BA value of the first peak group from the peaks included in the first peak group according to the window sizes and the time differences corresponding to the peaks included in the first peak group, and removing a second noise by subtracting the average BA value of the first peak group from the peaks included in the second peak group according to an average value of the window sizes and an average value of the time differences.

Generating the window sizes may comprise setting the window sizes to be triple the respective temporal distances between the positive peaks of the EKG signal and the negative peaks most close to the positive peaks of the EKG signal.

The positive peaks of the EKG signal may be allocated individually at a point being a first one-third portion of the corresponding window sizes.

Removing the first noise may comprise subtracting the average BA value of the first peak group of the window sizes corresponding to the peaks included in the first peak group from the peaks included in the first peak group by delaying the first peak group average BA value from the positive peaks of the EKG signal as much as the respective time differences.

BRIEF DESCRIPTION OF THE DRAWINGS

The implementation of this document will be described in detail with reference to the following drawings in which like numerals refer to like elements.

DETAILED DESCRIPTION

Hereinafter, an implementation of this document will be described in detail with reference to the attached drawings.

Figure 1:
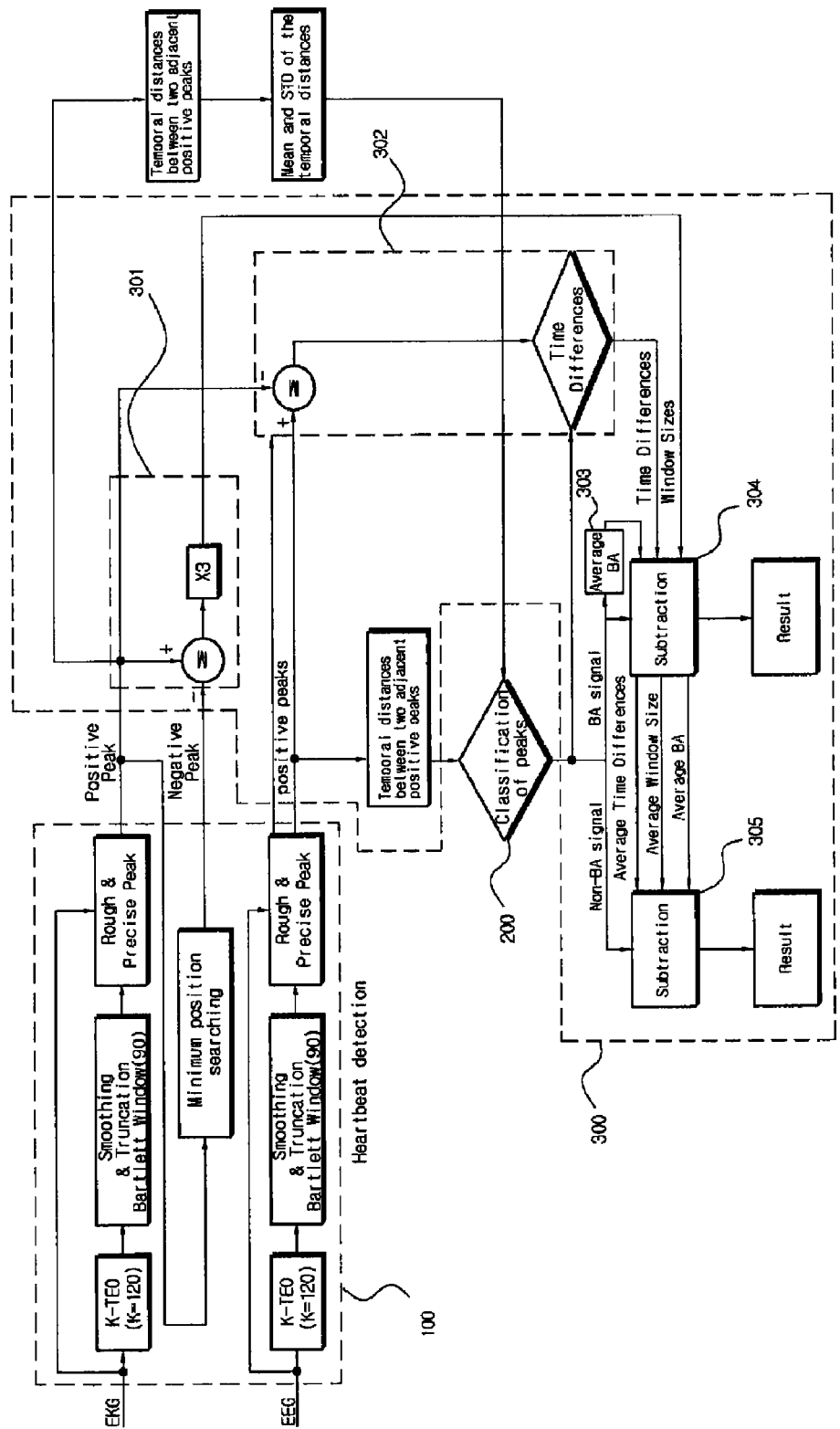
FIG. 1 is a diagram illustrating a brain wave measuring method according to an embodiment of the present invention.

FIG. 1 is a diagram illustrating a brain wave measuring method according to an embodiment of the present invention.

As illustrated, the brain wave measuring method includes a peak information extraction procedure 100, an EEG signal classification procedure 200, and a noise removal procedure 300.

<Peak Information Extraction Procedure>

In the peak information extraction procedure 100, positive peaks and negative peaks are extracted from an electrocardiogram (EKG) signal reflecting heartbeat information, and positive peaks are extracted from an electroencephalogram (EEG) signal reflecting heartbeat-caused noise information and brain wave information.

In the peak information extraction procedure 100, the positive peaks extracted from the EKG signal include R peaks. For instance, the R peaks may be extracted based on a k-TEO method. The negative peaks extracted from the EKG signal in the peak information extraction procedure 100 may be a minimum value between the two adjacent R peaks.

In general, one heartbeat generates P_QRS_T peaks. Among the P_QRS_T peaks, an R peak that has the largest positive value is determined as a positive peak of an EKG signal. This R peak is extracted using the aforementioned k-TEO method in which a peak is discovered based on a shape created at the peak generation moment. This R peak extraction can be defined based on the following equation.

$$\Psi_k x(n) = x^2(n) - x(n-k)x(n+k) \qquad \text{Eq. 1}$$

In the above equation, k is an empirical value and is measured at about 120. Among resultant values obtained from the application of an EKG signal to the above equation, a negative value is set at about 0, and then, applied to a Bartlett filter having a filter order of 90. Inflection points where slopes change from a positive value to a negative value are examined among resultant values from the Bartlett filter. The median value of those values corresponding to the respective inflection points is averaged to be used as a threshold value for finding an approximate R peak in the original EKG signal. On the basis of approximate R peaks found by a threshold value in the original EKG signal that is prior to the application of the k-TEO method, for instance, among values between 0.6 s prior to the approximate R peak and 0.6 s after the approximate R peak, the largest value is examined. The largest value is determined as an R peak.

In the case of an EKG signal, a negative peak that has the smallest value between the two adjacent R peaks is found to obtain a window size which will be described later. The negative peak found out as above represents a negative peak of the EKG signal.

In the case of an EEG signal, a procedure similar to the above described procedure of finding the R peak, which is the positive peak of the EKG signal, is performed to find out positive peaks of the EEG signal. Differently from the EKG signal, the window size is not examined in the EEG signal. Hence, the procedure of finding a negative peak is not performed.

<EEG Signal Classification Procedure>

In the EEG signal classification procedure 200, the positive peaks of the EEG signal are classified into a first peak group (i.e., BA signal group) and a second peak group (i.e., non-BA signal group) based on the positive peaks of the EKG signal. The first peak group is affected more greatly by a brain wave than by a heartbeat. In contrast, the second peak group is affected more greatly by the heartbeat than by the brain wave.

If the EEG signal is measured particularly in an MRI apparatus, the EEG signal includes a brain signal in addition to noise caused by the heartbeat. Thus, the positive peaks of the EEG signal are classified into the first peak group and the second peak group according to the determination whether the positive peaks are dominantly affected by BAs, which represent noise generated due to the heartbeat. Reference values that are used to classify the positive peaks of the EEG signal include an average value p of temporal distances between the adjacent R peaks of the EKG signal and a standard deviation value σ thereof. Table 1 below shows how the positive peaks of the EEG signal are classified.

TABLE 1

| $d_{i-1}$ | $d_i$ | Condition | Peak |
|---|---|---|---|
| R | R | | BA signal |
| R | IR | $\mu + \sigma < d_i$ | BA signal |
| | | $\mu + \sigma > d_i$ | Non-BA signal |

TABLE 1-continued

| $d_{i-1}$ | $d_i$ | Condition | Peak |
|---|---|---|---|
| IR | R | | Non-BA signal |
| IR | IR | | Non-BA signal |

In Table 1, d represents a temporal distance between the adjacent positive peaks of the EEG signal. With reference to Table 1, when d exists between the addition value of the average value μ of the temporal distances between the adjacent R peaks and the standard deviation value σ thereof and the subtraction value therebetween, it is determined as R. If d falls outside this given d value range, it is determined as IR. In the individual positive peaks of the EEG signal, $d_{i-1}$ representing a temporal distance between the reference positive peak and the prior positive peak, and $d_i$ representing a temporal distance between the reference positive peak and the post positive peak exist. The positive peaks of the EEG signal found using the two d values are classified into the first peak group and the second peak group according to the determination whether the positive peaks of the EEG signal are dominantly affected by the BAs, which represent noise generated due to the heartbeats. In the Table 1, the BA signal is included in the first peak group that is dominantly affected by the BAs, which represent heartbeat-caused noise, and the non-BA signal is included in the second peak group that is dominantly affected not by the BAs but by the brain signal.

<Noise Removal Procedure>

In the noise removal procedure 300, the noise according to the first peak group and the second peak group is removed from the EEG signal.

This noise removal procedure 300 includes generating window sizes 301, calculating time differences 302, calculating an average BA value of the first peak group 303, removing a first noise 304, and removing a second noise 305.

Figure 2:
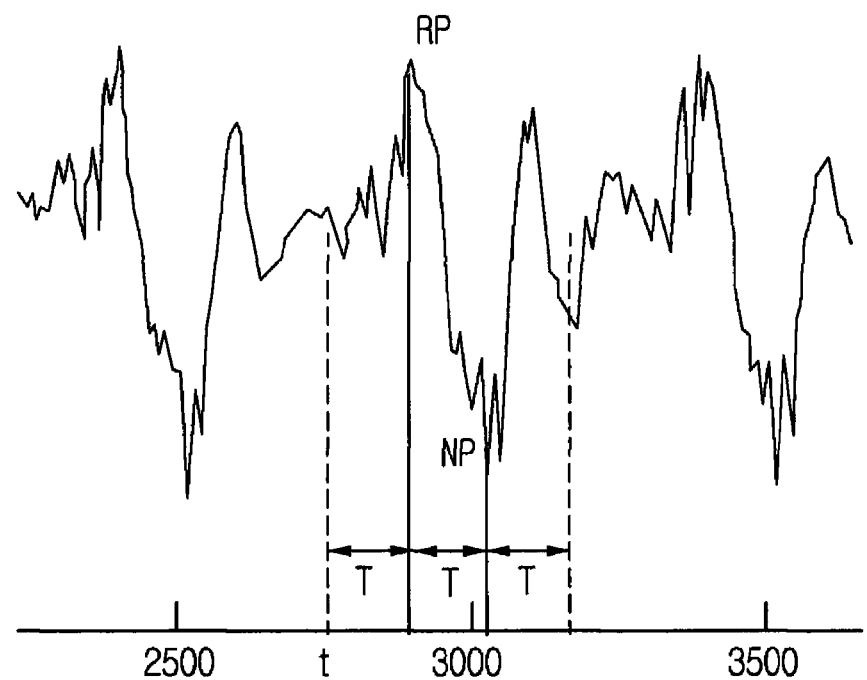
FIG. 2 illustrates a diagram illustrating different time differences between an electroencephalogram (EEG) signal and an electrocardiogram (EKG) signal.

In the window size generation operation 301, window sizes are generated over a time axis for every positive peak of the EKG signal based on the positive and negative peaks of the EKG signal. The window sizes may be triple the distances between the positive peaks of the EKG signal and the negative peaks most adjacent to the positive peaks over the time axis, and the positive peaks of the EKG signal may be allocated individually at a point that is a first one-third portion of the respective window sizes. A window size generation method will be described in detail with reference to FIG. 2. That is, a negative peak NP of an EKG signal that is most close to an R peak RP of the EKG signal is found. A window size is determined to be the triple of a temporal distance T between the R peak RP of the EKG signal and the negative peak NP of the EKG signal. Also, the R peak RP of the EKG signal is allocated at a point that is a first one-third portion of the window size, and the temporal distance T between a point t where the window starts and the R peak RP of the EKG signal is set to be ⅓ of the entire window size (i.e., 3T).

Figure 3:
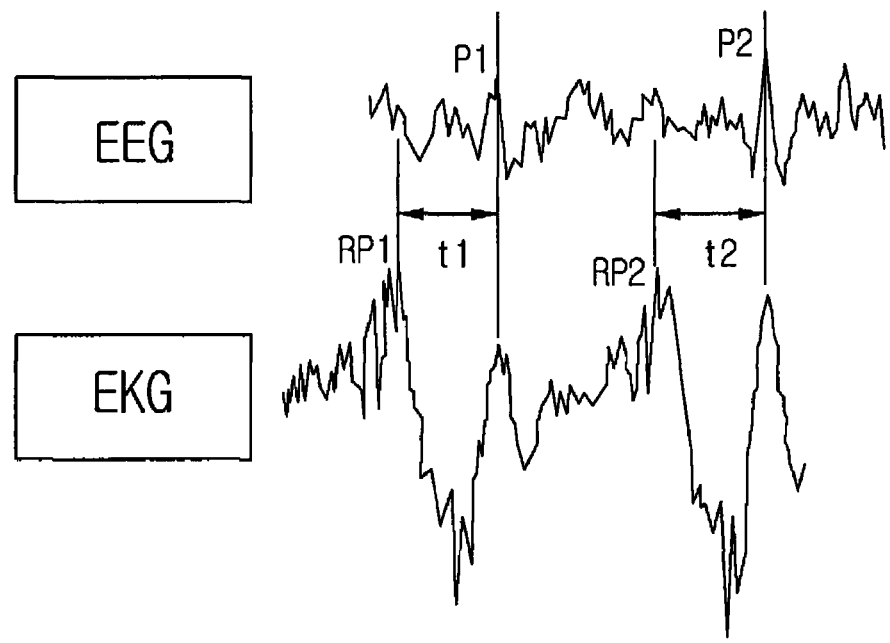
FIG. 3 is a diagram illustrating a window size.

In the time difference calculation operation 302, time differences between the peaks included in the first peak group and the positive peaks of the EKG signal temporally most close to the peaks included in the first peak group are calculated. With reference to FIG. 3, the time difference calculation method will be described in detail. Time differences are calculated for those peaks P1 and P2 included in a first peak group of an EEG signal (i.e., the peaks P1 and P2 that are dominantly affected by BAs, which represent noise generated due to the heartbeats). The time differences are obtained by finding the peaks P1 and P2 of the first peak group of the EEG signal temporally most close to R peaks RP1 and RP2 of an EKG signal, and calculating temporal distances t1 and t2 between the peaks P1 and P2 included in the first peak group of the EEG signal and the R peaks of the EKG signal temporally most close to the peaks P1 and P2.

In the first peak group average BA calculation operation 303, an average BA value of the peaks included in the first peak group is calculated. In detail, the average BA value of the peaks included in the first peak group is calculated using the time differences and the window sizes corresponding to the peaks of the first peak group dominantly affected by BAs, which represent noise generated by heartbeats. The window sizes corresponding to the peaks included in the first peak group have different values from each other. Thus, the maximum value of the window sizes is used as the window sizes to calculate the average BA value. If the window sizes are less than the maximum value, those window size values falling outside the window size are set at 0.

In the first noise removal operation 304, the average BA value of the first peak group is subtracted from the peaks included in the first peak group according to the time differences and the window sizes corresponding to the peaks included in the first peak group. More specifically, in the first noise removal operation 304, the first peak group average BA value with the window sizes corresponding to the peaks of the first peak group is subtracted from the peaks of the first peak group by delaying the first peak group average value from the positive peaks of the EKG signal as much as the respective time differences. In detail, BAs, which represent noise generated due to the heartbeats, are removed differently from the first peak group of the EEG signal and the second peak group of the second peak group. In the case of removing the BAs from the first peak group of the EEG signal, those values that are set at about 0 when the average BA value of the peaks included in the first peak group is calculated are removed.

In the second noise removal operation 305, the first peak group average BA value is subtracted from the peaks included in the second peak group according to an average value of the window sizes and an average value of the time differences in the first peak group. In the case of removing BAs, which represent heartbeat-caused noise, from the second peak group of the EEG signal, the average window size value and the average time difference value are used to remove the BAs instead of the adaptive window sizes and different time differences, which are used in removing the BAs from the first peak group of the EEG signal.

According to various embodiments of the present invention, BAs, which are noise components due to the heartbeats, can be effectively and easily removed when tests are performed using an EEG and fMRI as compared to the conventional BA removal method. A simultaneous test of an EEG and fMRI can proceed under recent development of technology. Despite this technical advancement, this test may not be immediately implemented in actual clinical fields due to the possibility of misdiagnosis for the case where BAs are not removed because the BAs often have a great impact on an EEG signal. However, the method according to the embodiments of the present invention allows an accurate diagnosis while removing the BAs. Thus, when software utilizing this suggested method is commercialized, high economical benefits can be achieved.

The brain wave measuring apparatus according to an embodiment of the present invention and a computer readable recording medium implemented with a program for executing the brain wave measuring method according to an embodiment of the present invention are replaced with the detailed description of the brain wave measuring method according to the embodiments of the present invention.

On the basis of various embodiments of the present invention, the measurement of a brain wave with a minimum distortion occurring due to heartbeat-caused noise can be performed.

Also, a generation of noise caused by heartbeats of a test object whose brain wave is measured using an MRI apparatus can be minimized.

Despite of irregularity in heartbeats, noise generated due to the heartbeat can be effectively removed.

Furthermore, an amount of computation during several procedures for removing heartbeat-caused noise can be reduced, so as to shorten a time taken for the brain wave measurement.

The invention being thus described, it will be obvious that the same may be varied in many ways. Such variations are not to be regarded as a departure from the spirit and scope of the invention and all such modifications as would be obvious to one skilled in the art are intended to be included within the scope of the following claims.

What is claimed is:

1. A method for measuring a brain wave comprising:
   extracting positive and negative peaks from an electrocardiogram (EKG) signal reflecting heartbeat information, and positive peaks from an electroencephalogram (EEG) signal reflecting heartbeat-caused noise information and brain wave information;
   classifying the positive peaks of the EEG signal into a first peak group and a second peak group based on the positive peaks of the EKG signal, wherein the first peak group is affected more greatly by the heartbeat than by the brain wave and the second peak group is affected more greatly by the brain wave than by the heartbeat; and
   removing noise from the EEG signal with a noise remover based on the classification, wherein noise is removed differently from the peaks of the first peak group than from the peaks of the second peak group.

2. The method of claim 1, wherein the positive peaks of the EKG signal include R peaks, the R peaks extracted by a k-TEO method.

3. The method of claim 2, wherein the negative peaks of the EKG signal have a minimum value between the two adjacent R peaks.

4. The method of claim 1, wherein classifying the EEG signal comprises classifying the positive peaks of the EEG signal into the first peak group and the second peak group according to an average value and a standard deviation of temporal distances between the adjacent positive peaks of the EKG signal.

5. The method of claim 1, wherein removing the noise comprises:
   generating window sizes over a time axis for every positive peak of the EKG signal based on the positive and negative peaks of the EKG signal;
   calculating time differences between the peaks included in the first peak group and the positive peaks of the EKG signal temporally most close to the peaks included in the first peak group;
   calculating an average value of ballistocardiac artifacts (BAs) of the peaks included in the first peak group;
   removing a first noise by subtracting the average BA value of the first peak group from the peaks included in the first peak group according to the window sizes and the time differences corresponding to the peaks included in the first peak group; and
   removing a second noise by subtracting the average BA value of the first peak group from the peaks included in the second peak group according to an average value of the window sizes and an average value of the time differences.

6. The method of claim 5, wherein generating the window sizes comprises setting the window sizes to be triple the respective temporal distances between the positive peaks of the EKG signal and the negative peaks most close to the positive peaks of the EKG signal.

7. The method of claim 6, wherein the positive peaks of the EKG signal are allocated individually at an approximate point being a first one-third portion of the corresponding window sizes.

8. The method of claim 5, wherein removing the first noise comprises subtracting the average BA value of the first peak group with the window sizes corresponding to the peaks included in the first peak group from the peaks included in the first peak group by delaying the first peak group average BA value from the positive peaks of the EKG signal as much as the respective time differences.

9. An apparatus for measuring a brain wave, comprising:
   a peak information extractor extracting positive and negative peaks from an electrocardiogram (EKG) signal reflecting heartbeat information, and positive peaks from an electroencephalogram (EEG) signal reflecting heartbeat-caused noise information and brain wave information;
   an EEG signal classifier classifying the positive peaks of the EEG signal into a first peak group and a second peak group based on the positive peaks of the EKG signal, wherein the first peak group is affected more greatly by the heartbeat than by the brain wave and the second peak group is affected more greatly by the brain wave than by the heartbeat; and
   a noise remover removing noise from the EEG signal based on the classification, wherein noise is removed differently from the peaks of the first peak group than from the peaks of the second peak group.

10. The apparatus of claim 9, wherein the positive peaks of the EKG signal include R peaks, the R peaks extracted by a k-TEO method.

11. The apparatus of claim 10, wherein the negative peaks of the EKG signal have a minimum value between the two adjacent R peaks.

12. The apparatus of claim 9, wherein the EEG signal classifier classifies the positive peaks of the EEG signal into the first peak group and the second peak group according to an average value and a standard deviation of temporal distances between the adjacent positive peaks of the EKG signal.

13. The apparatus of claim 9, wherein the noise remover comprises:
   a window size generation block generating window sizes over a time axis for every positive peak of the EKG signal based on the positive and negative peaks of the EKG signal;
   a time difference calculation block calculating time differences between the peaks included in the first peak group and the positive peaks of the EKG signal temporally most close to the peaks included in the first peak group;
   an average ballistocardiac artifact (BA) calculation block calculating an average value of BAs of the peaks included in the first peak group;
   a first noise removal block removing a first noise by subtracting the average BA value of the first peak group from the peaks included in the first peak group according to the window sizes and the time differences corresponding to the peaks included in the first peak group; and a second noise removal block removing a second noise by subtracting the average BA value of the first peak group from the peaks included in the second peak group according to an average value of the window sizes and an average value of the time differences.

14. The apparatus of claim 13, wherein the window sizes generated in the window size generation block are triple the respective temporal distances between the positive peaks of the EKG signal and the negative peaks most close to the positive peaks of the EKG signal.

15. The apparatus of claim 14, wherein the positive peaks of the EKG signal are allocated individually at an approximate point being a first one-third portion of the corresponding window sizes.

16. The apparatus of claim 13, wherein the first noise removal block subtracting the average BA value of the first peak group with the window sizes corresponding to the peaks included in the first peak group from the peaks included in the first peak group by delaying the first peak group average BA value from the positive peaks of the EKG signal as much as the respective time differences.

17. A computer readable recording medium implemented with a program for executing a brain wave measuring method, the computer readable recording medium comprising:

a first instruction of extracting positive and negative peaks from an electrocardiogram (EKG) signal reflecting heartbeat information, and positive peaks from an electroencephalogram (EEG) signal reflecting heartbeat-caused noise information and brain wave information;

a second instruction of classifying the positive peaks of the EEG signal into a first peak group and a second peak group based on the positive peaks of the EKG signal, wherein the first peak group is affected more greatly by the heartbeat than by the brain wave and the second peak group is affected more greatly by the brain wave than by the heartbeat; and a third instruction of removing noise from the EEG signal based on the classification, wherein noise is removed differently from the peaks of the first peak group than from the peaks of the second peak group.

18. The computer readable recording medium of claim 17, wherein the positive peaks of the EKG signal include R peaks, the R peaks extracted by a k-TEO method.

19. The computer readable recording medium of claim 18, wherein the negative peaks of the EKG signal have a minimum value between the two adjacent R peaks.

20. The computer readable recording medium of claim 17, wherein the second instruction of classifying the EEG signal comprises classifying the positive peaks of the EEG signal into the first peak group and the second peak group according to an average value and a standard deviation of temporal distances between the adjacent positive peaks of the EKG signal.

21. The computer readable recording medium of claim 17, wherein the third instruction of removing the noise comprises:

generating window sizes over a time axis for every positive peak of the EKG signal based on the positive and negative peaks of the EKG signal;

calculating time differences between the peaks included in the first peak group and the positive peaks of the EKG signal temporally most close to the peaks included in the first peak group;

calculating an average value of ballistocardiac artifacts (BAs) of the peaks included in the first peak group;

removing a first noise by subtracting the average BA value of the first peak group from the peaks included in the first peak group according to the window sizes and the time differences corresponding to the peaks included in the first peak group; and removing a second noise by subtracting the average BA value of the first peak group from the peaks included in the second peak group according to an average value of the window sizes and an average value of the time differences.

22. The computer readable recording medium of claim 21, wherein generating the window sizes comprises setting the window sizes to be triple the respective temporal distances between the positive peaks of the EKG signal and the negative peaks most close to the positive peaks of the EKG signal.

23. The computer readable recording medium of claim 22, wherein the positive peaks of the EKG signal are allocated individually at a point being a first one-third portion of the corresponding window sizes.

24. The computer readable recording medium of claim 21, wherein removing the first noise comprises subtracting the average BA value of the first peak group with the window sizes corresponding to the peaks included in the first peak group from the peaks included in the first peak group by delaying the first peak group average BA value from the positive peaks of the EKG signal as much as the respective time differences.

* * * * *